US006974423B2

(12) United States Patent
Zurcher

(10) Patent No.: US 6,974,423 B2
(45) Date of Patent: Dec. 13, 2005

(54) NEEDLE ASSEMBLY

(75) Inventor: Robert Zurcher, Little Falls, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 126 days.

(21) Appl. No.: 10/365,760

(22) Filed: Feb. 12, 2003

(65) Prior Publication Data

US 2003/0171695 A1 Sep. 11, 2003

Related U.S. Application Data

(60) Provisional application No. 60/363,362, filed on Mar. 11, 2002.

(51) Int. Cl.[7] ............................................. A61B 5/00
(52) U.S. Cl. ...................... 600/576; 600/573; 604/192; 604/403; 604/412
(58) Field of Search ............................. 600/573, 576, 600/577, 579, 582, 583; 604/403, 110, 411–415, 604/205, 272, 181, 187, 191, 192, 197, 198, 604/218, 230, 263, 404

(56) References Cited

U.S. PATENT DOCUMENTS

| | | | | |
|---|---|---|---|---|
| 5,085,640 A | * | 2/1992 | Gibbs | 604/110 |
| 5,263,942 A | | 11/1993 | Smedley et al. | |
| 5,531,694 A | * | 7/1996 | Clemens et al. | 604/110 |
| 5,709,667 A | * | 1/1998 | Carilli | 604/198 |
| 5,800,395 A | * | 9/1998 | Botich et al. | 604/110 |
| 5,897,508 A | * | 4/1999 | Konrad | 600/573 |
| 6,063,040 A | * | 5/2000 | Owen et al. | 600/573 |
| 2003/0060760 A1 | * | 3/2003 | Botich et al. | 604/110 |

FOREIGN PATENT DOCUMENTS

| EP | 1 027 864 A1 | 8/2000 |
|---|---|---|
| WO | WO 98/24493 | 6/1998 |

* cited by examiner

*Primary Examiner*—Charles Marmor
(74) *Attorney, Agent, or Firm*—Gerald E. Hespos, Esq.; Mark Lindsey

(57) ABSTRACT

A blood collection needle assembly includes a holder body having a tube receiving chamber and a needle receiving chamber. A proximal needle is mounted to the holder body and projects into the tube receiving chamber. A distal needle is slidably mounted in alignment with the needle receiving chamber. A spring is provided to urge distal needle into the needle receiving chamber, and a trigger is provided for selectively permitting or preventing proximal movement of the distal needle. A transverse passage between the two needles is formed from a transparent material and provides indication of venus axis. The blood collection needle assembly is used to collect a sample of blood in a conventional manner. After collection of the blood, the trigger is actuated to release the distal needle and the spring propels the distal needle in a proximal direction for safe shielding within the needle receiving chamber of the holder body.

8 Claims, 5 Drawing Sheets

NEEDLE ASSEMBLY

RELATED APPLICATIONS

This application claims priority on U.S. Provisional Patent Appl. No. 60/363,362 filed Mar. 11, 2002.

BACKGROUND OF THE INVENTION

1. Field of the Invention

The subject invention relates to a needle assembly for collecting samples of fluid from a patient. The needle assembly includes a needle holder and a needle cannula that can be retracted into the holder after use.

2. Description of the Related Art

A needle assembly is used to acquire a sample of blood from a patient and to deposit the blood sample in an evacuated tube. The tube then is shipped from the site of collection to a laboratory for analysis.

The typical prior art needle assembly includes a needle holder that has opposed proximal and distal ends and a tubular side wall extending between the ends. The proximal end of the needle holder is widely open. However, a wall extends partially across the distal end of the tubular side wall. A needle cannula is mounted to the distal end wall of the prior art needle holder. The needle cannula includes a pointed distal end that extends distally beyond the needle holder and a pointed proximal end that extends centrally within the tubular side wall of the holder.

The prior art blood collection needle assembly is employed by a phlebotomist who aligns the pointed distal end of the needle cannula with a targeted blood vessel. The phlebotomist then gently eases the pointed distal end of the needle cannula into the blood vessel in a procedure referred to as venipuncture. Most phlebotomists prefer to align the blood collection needle assembly such that the beveled distal end of the needle cannula faces up. Thus, the phlebotomist can visually identify the tip of the needle cannula and can properly align the tip with targeted blood vessel. Additionally, most phlebotomists prefer to have the needle cannula aligned at a very small acute angle to the skin surface of the patient. The small acute angle facilitates visual alignment of the needle cannula with the targeted blood vessel and further helps the phlebotomist to gauge the depth of insertion of the needle cannula.

The phlebotomist urges an evacuated tube into the open proximal end of the needle holder after the targeted blood vessel has been accessed by the needle cannula. The evacuated tube is moved sufficiently into the needle holder for the pointed proximal end of the needle cannula to pierce the rubber seal that extends across the mouth of the evacuated tube. Thus, blood from the targeted blood vessel will flow through the needle cannula and into the evacuated tube. This flow of blood into the evacuated tube often is the first indication that the targeted blood vessel has been accessed. Unfortunately this initial observable flow of blood may not appear until several seconds after the venipuncture attempt. On some occasions, the phlebotomist may incorrectly interpret this elapsed time as an indication that the targeted blood vessel has been missed. Thus, a phlebotomist may withdraw the needle cannula and conduct the venipuncture procedure again, thereby causing additional discomfort and trauma for the patient.

Some prior art blood collection needle assemblies are constructed with a transparent flashback chamber for receiving the blood prior to flow of the blood into the evacuated tube. Thus, the flashback chamber can provide an earlier visual indication of successful venipuncture. However, the flashback chamber substantially complicates the prior art blood collection needle assembly and typically will increase both the cost and the size of the prior art blood collection needle assembly.

The tubular needle holder for the prior art blood collection needle assembly typically is about 2 cm in diameter. Additionally, both the proximal and distal portions of the needle cannula are aligned along the axis of the prior art tubular needle holder. Thus, the needle cannula is spaced radially from the tubular side wall of the needle holder by approximately 1 cm. This relatively large radial dimension prevents the phlebotomist from aligning the needle cannula at a very small acute angle during venipuncture. Thus, the standard blood collection needle assembly must be aligned at an acute angle that is larger than the angle preferred by most phlebotomists.

An accidental stick with a used needle cannula can be very painful and can transmit disease. Consequently, most prior art blood collection needle assemblies are constructed to reduce the risk of accidental needle sticks. For example, some prior art blood collection needle assemblies have actuators that enable the used needle cannula to be released from the needle holder and into a sharps receptacle without manually unthreading the needle cannula from the needle holder. Other prior art blood collection needle assemblies have a shield that can be moved distally along the needle cannula or that can be rotated into surrounding relationship with the needle cannula. Many prior art shields add to the cross-sectional dimensions of the needle holder, and hence further increase the minimum possible acute angle alignment of the needle cannula for venipuncture. Some prior art shields for blood collection needle assemblies visually obscure the distal end of the needle cannula and/or the evacuated tube. Hence, these prior art shields can impede the view of the collected blood that is required to assure a successful venipuncture. Other prior art shields are sufficiently cumbersome that the phlebotomist may defer employing the shield, thereby creating a significant risk for an accidental needle stick.

In view of the above, an object of the invention is to provide a blood collection needle assembly that has the distally directed needle cannula positioned and aligned to facilitate venipuncture.

Another object of the invention is to provide a blood collection needle assembly with a blood flashback indication to provide accurate and early evidence of an acceptable venipuncture.

A further object of the invention is to provide a blood collection needle assembly that enables an efficient and safe shielding of the needle cannula.

SUMMARY OF THE INVENTION

The subject invention is directed to a blood collection needle assembly. The assembly includes a needle holder that has an elongate body with opposed proximal and distal ends and a blood collection tube chamber extending between the ends. The blood collection tube chamber is open at the proximal end of the body and extends substantially to the distal end of the body. A distal wall partly closes the blood collection tube chamber at the distal end of the body, but includes an aperture that extends axially into the blood collection tube chamber. The body further includes a used needle chamber substantially adjacent the blood collection tube chamber. The used needle chamber has an open distal end and a closed proximal end. However, a vent may communicate with the proximal end of the used needle chamber.

The blood collection needle assembly of the subject invention further includes a proximal needle cannula mounted to the distal wall of the body and extending into the blood collection tube chamber. The proximal needle cannula includes a sharply pointed proximal end disposed within the blood collection tube chamber and lumen that communicates with both the aperture in the distal wall and with the blood collection tube chamber. A needle-pierceable elastomeric multiple sample sheath may be mounted over the proximal needle cannula, substantially as in prior art needle holders. Thus, an evacuated tube can be urged distally into the open proximal end of the blood collection tube chamber. Sufficient movement of the evacuated tube will cause the rubber stopper that extends across the open end of the evacuated tube to engage the needle-pierceable multiple sample sheath that surrounds the proximal needle of the assembly. Further movement of the evacuated tube will cause the pointed end of the proximal needle to pierce through the elastomeric sheath and through the rubber stopper of the evacuated tube. Thus, the lumen of the proximal needle cannula can be placed in communication with the evacuated blood collection tube substantially as in the prior art.

The blood collection tube assembly of the subject invention further includes a distal cap securely mounted across the distal wall of the body. The cap and the distal wall of the body cooperate to define a transverse channel that extends from the aperture in the distal wall to the open distal end of the used needle chamber.

The blood collection tube assembly further includes a distal needle cannula having a prixmal end, a pointed distal end and a lumen extending therebetween. The distal needle cannula is mounted for controlled movement into the used needle chamber. Additionally, the proximal end of the distal needle cannula is configured to communicate with the transverse passage defined between the distal wall of the body and the cap of the needle holder. Thus, communication between the lumen of the distal needle cannula and the lumen of the proximal needle cannula can be achieved through the transverse passage.

The cap preferably is transparent. Thus, blood flowing through the transverse passage will be readily visible at the distal end of the needle holder. Accordingly, the blood collection needle assembly provides a clear indication that the blood vessel has been accessed properly. This venous indication will occur well before the blood flows into the evacuated tube.

A biasing means may be provided for biasing the distal needle cannula in a proximal direction and into the used needle chamber formed in the body. The biasing means may be a coil spring concentrically surrounding the distal needle cannula and disposed within a portion of the cap.

The blood collection needle assembly may further include a trigger that is selectively actuatable from a location externally of the needle holder. The trigger may be operative to hold the distal needle cannula in a distal position for collecting a sample of blood from a patient. The trigger then may be moved to a second position for releasing the distal needle and enabling the biasing means to propel the distal needle cannula in a proximal direction and into a position where the distal needle cannula is safely enclosed within the used needle chamber.

Communication between the distal needle cannula and the transverse passage may be provided by a transverse aperture near the proximal end of the distal needle cannula. A pair of seals may be mounted in spaced relationship around the distal needle cannula to prevent errant flow of blood from the distal needle cannula. One seal may be disposed to lie proximally of the transverse passage when the distal needle cannula is in the distal position. The second seal may be disposed distally of the transverse passage when the distal needle cannula is in its distal position. Thus, blood flowing through the lumen of the distal needle cannula will be channelized by the seals into the transverse passage and toward the proximal needle cannula.

The blood collection needle assembly of the subject invention provides the distal needle cannula at an offset or transverse position on the body of the needle holder. Thus, a phlebotomist can align the distal needle cannula at a very small acute angle to the skin of the patient during venipuncture.

Additionally, the blood collection needle assembly of the subject invention enables automatic shielding to occur without complex telescoping or pivoting shields and immediately upon withdrawal of the distal needle from the patient. Hence, a very high degree of safety can be achieved without complex mechanisms that could impede normal usage of the assembly.

The seals around the distal needle cannula can affect the speed of withdrawal of the distal needle cannula into the used needle chamber. More particular, the seals may cause air in the used needle chamber to compress and resist the proximal movement of the distal needle cannula. To facilitate proximal movement of the distal needle cannula into the used needle chamber, a vent may be provided at a proximal position in the used needle chamber. The vent can be formed from a material with a selected air flow rate to achieve a desired rate of acceleration of the distal needle cannula into the used needle chamber.

DETAILED DESCRIPTION

Figure 1:
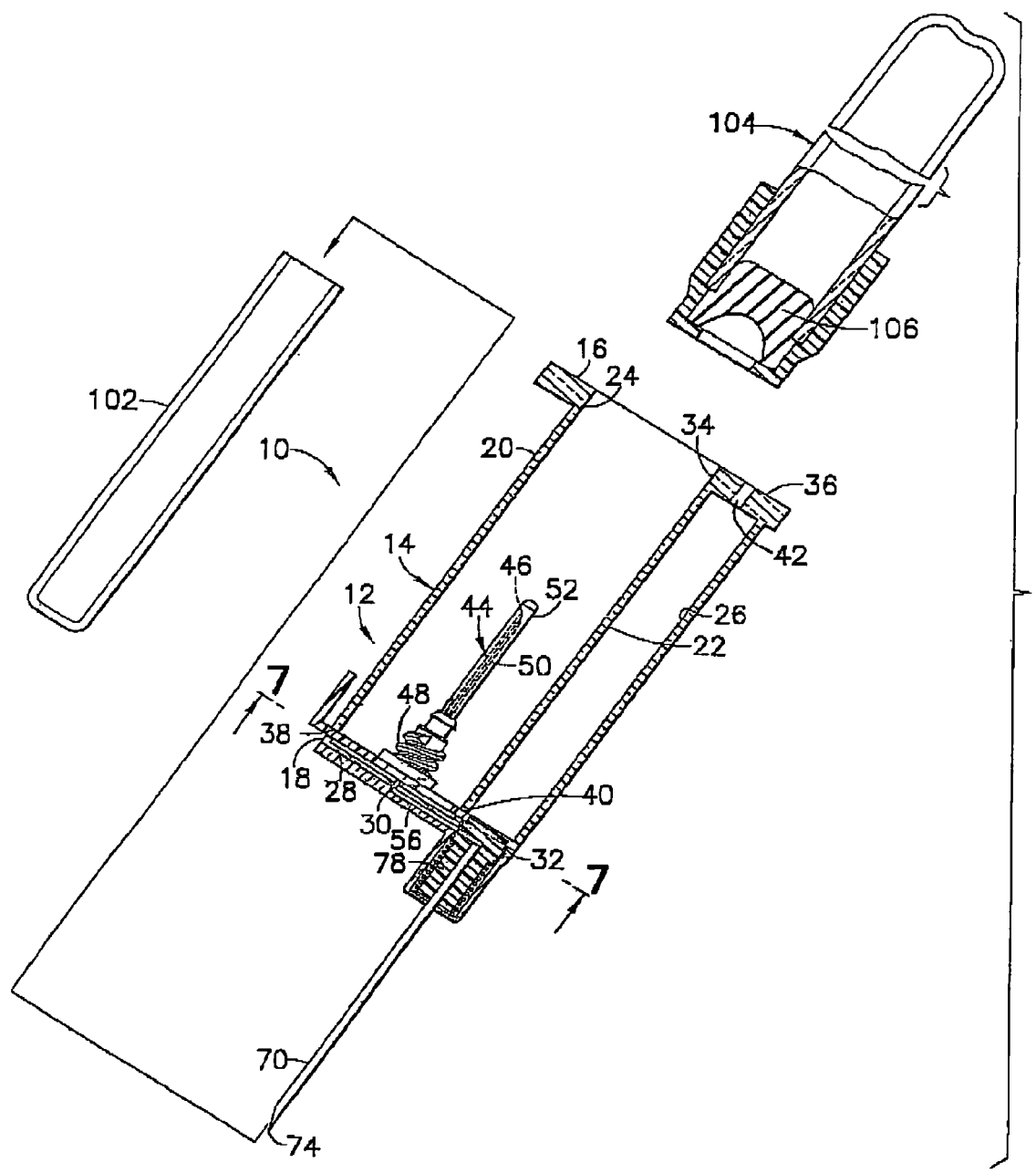
FIG. 1 is a longitudinal cross-sectional view of a blood collection needle assembly prior to use.

A blood collection needle assembly in accordance with the invention is identified generally by the numeral 10 in FIGS. 1–4. Blood collection needle assembly 10 includes a holder assembly 12 for holding needles and an evacuated blood collection tube. Holder assembly 12 includes a body 14 with a proximal end 16, an opposed distal end 18 and a tubular outer wall 20 extending between proximal end 16 and distal end 18. Holder body 14 further includes a transverse inner wall 22 extending substantially from proximal end 16 to distal end 18 and connecting spaced apart regions on tubular outer wall 20. Outer wall 20 and inner wall 22 cooperate to define a cylindrical tube receiving chamber 24 and a cylindrical needle receiving chamber 26 in bolder body 14.

Holder body 14 is characterized further by a distal wall 28 extending across distal end 18 of holder body 14. Distal wall 28 is characterized by aperture 30 substantially centrally aligned with tube receiving chamber 24 and an opening 32 substantially centrally aligned with needle receiving chamber 26.

Proximal end 16 of holder body 14 defines a wide opening 34 into tube receiving chamber 24. Opening 34 is dimensioned to slidably receive an evacuated blood collection tube as explained further herein. Proximal end 16 of holder body 14 further includes a proximal wall 36 closing the proximal end of needle receiving chamber 26.

Outer wall 20 of holder body 14 includes a transverse slot 38 extending therethrough and communicating with portions of tube receiving chamber 24 adjacent distal end wall 28. Additionally, inner wall 22 includes a transverse slot 40 substantially adjacent distal end wall 28. Slots 38 and 40 are aligned and are dimensioned to receive a trigger as explained further herein.

Proximal wall 36 further includes a vent 42 extending therethrough and communicating with needle receiving chamber 26. Vent 42 enables a controlled escape of air from needle receiving chamber 26 for controlling the speed of movement of the distal needle into needle receiving chamber 26, as explained further herein.

Blood collection needle assembly 10 further includes a proximal needle cannula 44 with a pointed proximal end 46, a distal end 48 and a lumen 50 extending therebetween. Distal end 48 of proximal needle 44 is mounted to distal wall 28 of holder body 14 such that lumen 50 communicates wit aperture 30 and such that proximal needle cannula 44 extends centrally in tube receiving chamber 24. An elastomeric needle pierceable multiple sample sleeve 52 is securely mounted over proximal needle cannula 44. Sleeve 52 seals the lumen through proximal needle cannula 44. However, forces exerted by the stopper of an evacuated blood collection tube will deflect sleeve 52 sufficiently for pointed proximal end 46 of proximal needle cannula 44 to pierce through sleeve 52 and through the rubber stopper of the evacuated blood collection tube.

Figure 6:
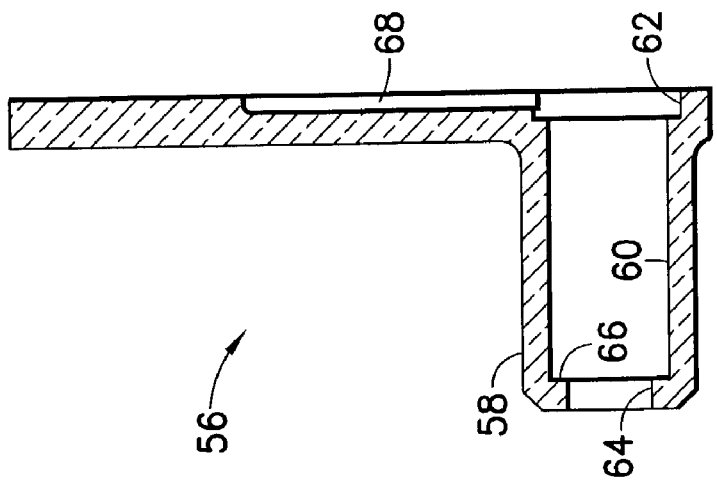
FIG. 6 is a cross-sectional view taken along line 6—6 in FIG. 5.
Figure 5:
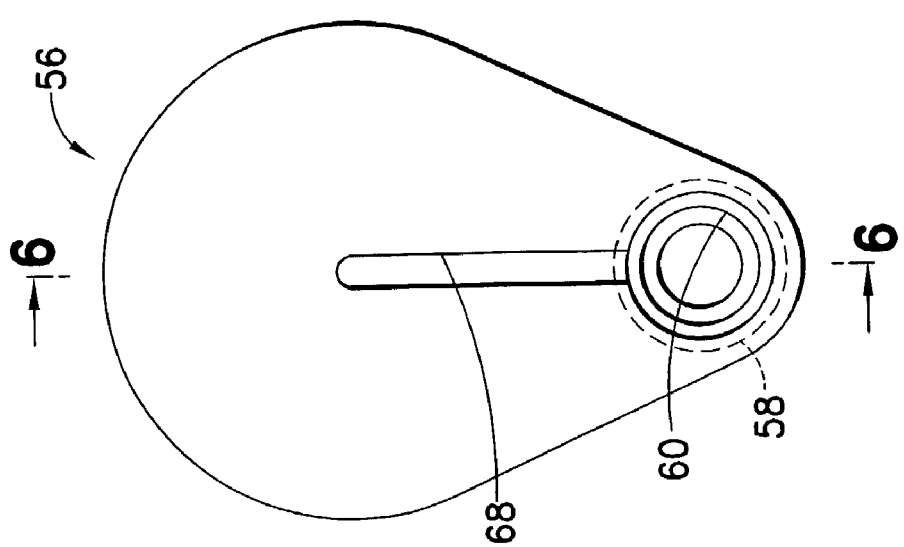
FIG. 5 is a plan view showing the surface of the cap that faces the body of the needle holder.
Figure 7:
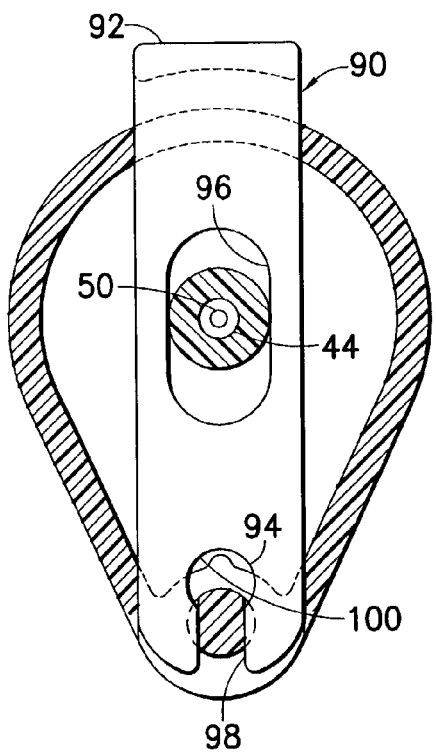
FIG. 7 is a cross-sectional view taken along line 7—7 in FIG. 1 and showing the trigger in a first operational position.

The blood collection needle assembly 10 further includes a transparent cap 56 mounted to distal wall 28 of holder body 14. As shown in FIG. 6, cap 56 includes a generally tubular nose 58 having a needle mounting chamber 60 therein. Needle mounting chamber 60 includes an open proximal end 62 disposed to align with opening 32 in distal end wall 28 of holder body 14 and also to align with needle receiving chamber 26 in holder body 14. Needle mounting chamber 60 further includes a distal opening 64 dimensioned to slidably receive a needle cannula as explained further below. Distal opening 64 is cross-sectionally smaller than intermediate portions of needle mounting chamber 60, and hence an annular stop rim 66 is defined adjacent distal opening 64.

Cap 56 further includes a transverse passage 68 extending from needle mounting chamber 60 to aperture 30 in distal wall 28 of holder body 14. Transverse passage 68 thus provides communication between needle mounting chamber 60 and aperture 30 in distal wall 28 of holder body 14. As noted above, aperture 30 in distal end wall 28 of holder body 14 provides communication with lumen 50 of proximal needle cannula 44. Hence, passage 68 provides communication between needle mounting chamber 60 and lumen 50 of proximal needle cannula 44.

Blood collection needle assembly 10 further includes a distal needle cannula 70 with a proximal end 72, a pointed distal end 74 and a lumen 76 extending therebetween. Proximal end 72 of distal needle cannula 70 is mounted to a hub 78 that is disposed for sliding sealed engagement in needle mounting channel 60 of cap 56 and in opening 32 in distal end wall 28 of holder body 14. More particularly, hub 78 includes a proximal seal 80 disposed proximally of transverse passage 68 and a distal seal 82 disposed distally of transverse passage 68. Additionally, hub 78 includes a transverse aperture 84 between seals 80 and 82. Transverse aperture 84 provides fluid communication between lumen 76 of distal needle cannula 70 and transverse passage 68 in cap 56. As shown in FIGS. 1–4 distal needle cannula 70 is substantially parallel to and offset from proximal needle cannula 44.

A coil spring 86 concentrically surrounds distal needle cannula 70 and has a proximal end engaged with hub 78 and a distal end engaged with stop rim 66 in nose 58 of cap 56.

Distal needle cannula 70 can be telescoped between distal and proximal positions relative to both needle mounting chamber 60 and needle receiving chamber 26. More particularly, in the distal position, shown in FIG. 1, hub 78 is disposed substantially within needle mounting chamber 60 and adjacent opening 32, and distal end 74 of distal needle cannula 70 projects distally beyond nose 58 of cap 56. In this distal position, coil spring 86 is maintained in a compressed condition. However, coil spring 86 can propel distal needle cannula 70 in a proximal direction such that needle hub 78 and distal end 74 of needle cannula 70 are disposed safely within needle receiving chamber 26 and needle mounting chamber 60.

Figure 8:
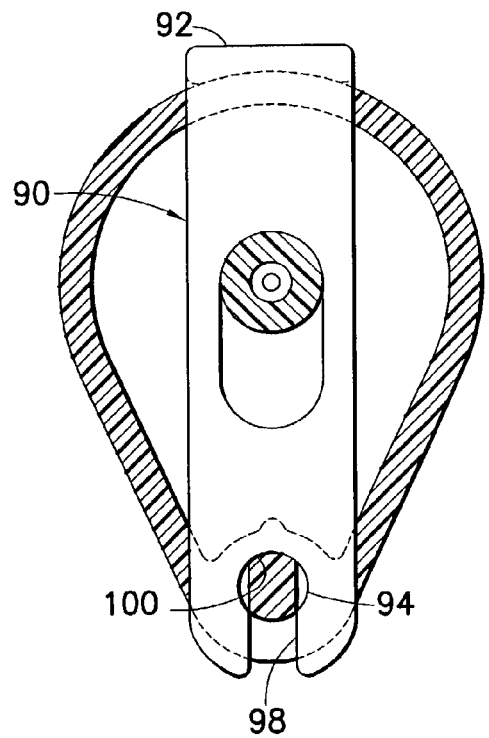
FIG. 8 is a cross-sectional view similar to FIG. 7, but showing the trigger in an operational position for permitting withdrawal of the distal needle cannula into the needle chamber of the body.
Figure 9:
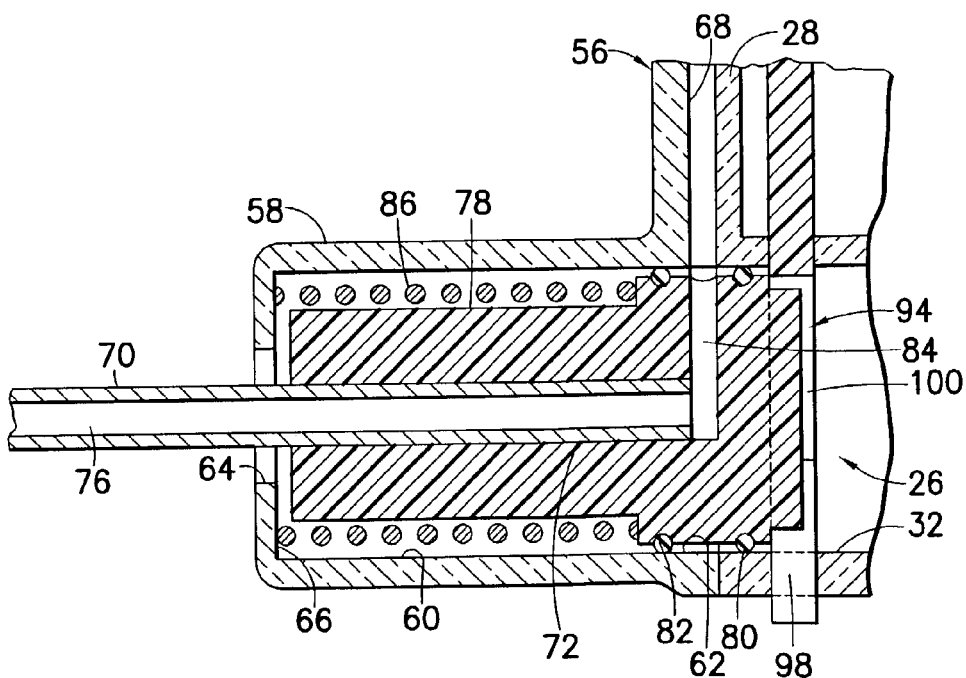
FIG. 9 is a schematic cross-sectional view showing the seals disposed adjacent the proximal end of the distal needle cannula.

Blood collection needle assembly 10 further includes a trigger 90 mounted in slots 38 and 40 of holder body 14. Trigger 90 includes an actuator surface 92 disposed externally of holder body 14. Additionally, trigger 90 includes a stepped locking aperture 94 and an elongate aperture 96 between stepped locking aperture 94 and actuator 92. Stepped locking aperture 94 includes a small diameter portion 98 at a location on trigger 90 furthest from actuator 92 and a large diameter portion 100 closer to actuator 92. Trigger 90 can be moved transversely of holder body 14 from a first position shown in FIG. 1 to a second position shown in FIG. 4. In the first position, an end of elongate aperture 96 furthest from actuator 92 is aligned with proximal needle cannula 44, and small diameter portion 98 of locking aperture 94 aligns with proximal the end of hub 78 on distal needle cannula 70. Small diameter portion 98 of locking aperture 94 is dimensioned to prevent passage of the assembly of needle cannula 70 and hub 78 into needle receiving chamber 26. However, digital pressure on actuator 92 moves trigger 90 transversely into the position of FIGS. 4 and 8. In this position, the end of elongate central aperture 96 closest to actuator 92 will align with proximal needle cannula 44. Additionally, in this position large diameter portion 100 of locking aperture 94 will align with hub 78 of distal needle cannula 70. Large diameter portion 100 of locking aperture 94 is dimensioned to permit passage of hub 78 of distal needle cannula 70 into needle receiving chamber 26. Consequently, the assembly of needle cannula 70 and hub 78 will be propelled under the action of coil spring 86 into needle receiving chamber 26. As a result, pointed distal end 74 of distal needle cannula 70 will be safely retained within needle receiving chamber 26 or needle mounting chamber 60.

Figure 2:
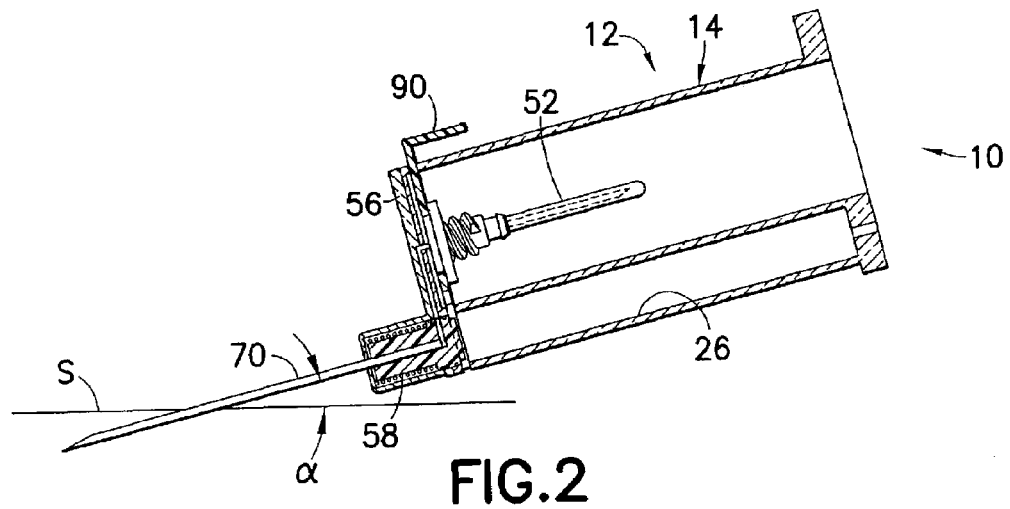
FIG. 2 is a longitudinal cross-sectional view of the blood collection needle assembly after removal of the safety shield and prior to insertion of the evacuated tube into the tube receiving chamber.
Figure 4:
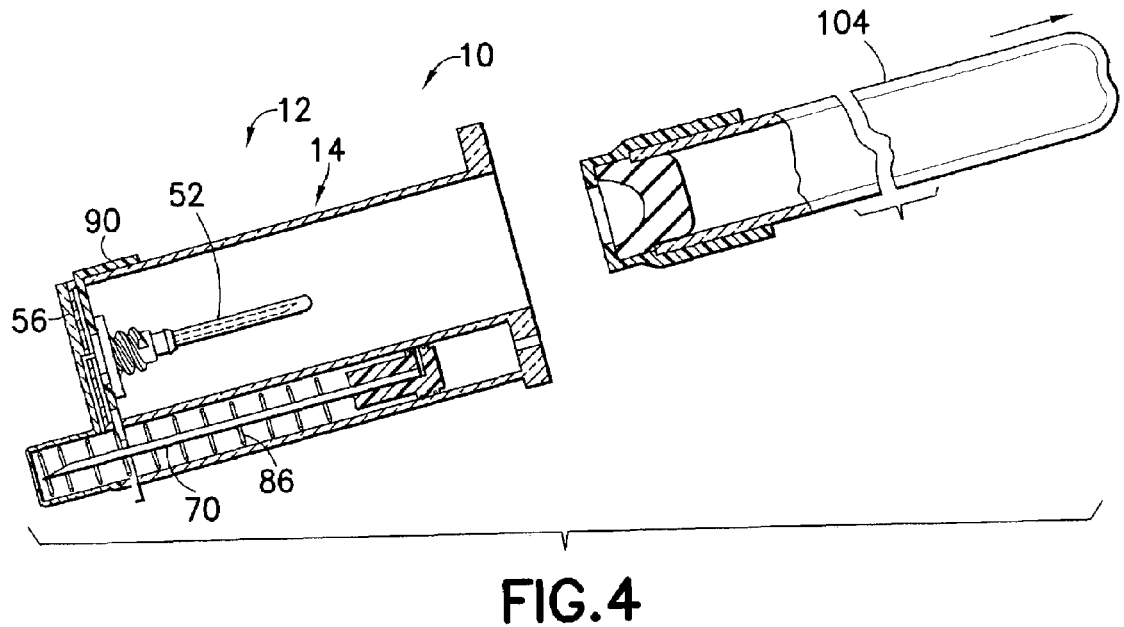
FIG. 4 is a longitudinal exploded cross-sectional view showing the blood collection needle assembly after completion of venipuncture and shielding of the distal needle cannula.
Figure 3:
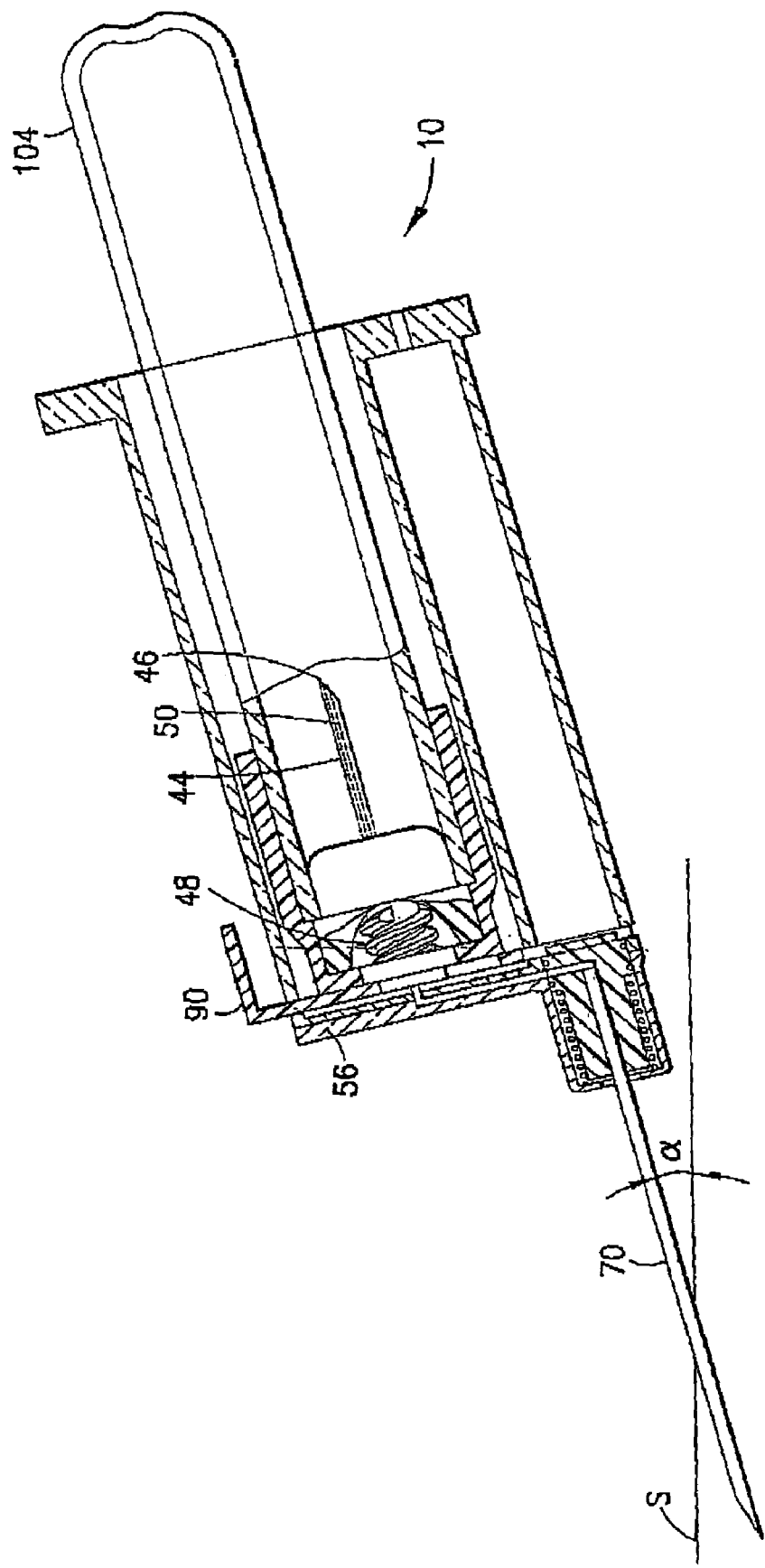
FIG. 3 is a longitudinal cross-sectional view during venipuncture.

The blood collection needle assembly is shipped substantially in the condition shown in FIG. 1, including a rigid safety shield 102 mounted over distal needle cannula 70 and removably engaged with nose 58 of cap 56. Blood collection needle assembly 10 is used by initially removing safety shield 102 to expose distal needle cannula 70. The phlebotomist then conducts a venipuncture procedure by aligning pointed distal end 74 of distal needle cannula 70 with a targeted blood vessel, and piercing the skin S and adjacent bodily tissue to access the targeted blood vessel, as shown in FIG. 2. The alignment of distal needle cannula 70 with the targeted blood vessel is facilitated due to the offset position of distal needle cannula 70 relative to holder body 14. In particular, the offset position of distal needle cannula 70 permits the phlebotomist to hold distal needle cannula 70 at a very small acute angle a relative to the skin of the patient.

Upon successful venipuncture, blood will flow through the lumen of distal needle cannula 70, through transverse aperture 84 in needle hub 78 and into transverse passage 68 of transparent cap 56. The transparency of cap 56 enables visual confirmation of the presence of blood in transverse passage 68, and hence provides a positive confirmation of successful venipuncture. Furthermore, the close proximity of transverse passage 68 to lumen 76 in distal needle cannula 70 ensures that the venipuncture indication is provided very quickly after the successful venipuncture has been achieved.

A phlebotomist may sequentially insert and remove several evacuated tubes 104 into tube receiving chamber 24 of holder body 14. More particular, evacuated tubes 104 are advanced sufficiently into tube receiving chamber 24 for stopper 106 on evacuated tube 104 to engage multiple sample sleeve 52 on proximal needle cannula 14. Continued distal movement of evacuated tube 104 into tube receiving chamber 24 collapses sleeve 52 and causes proximal point 46 on proximal needle cannula 44 to pierce through both sleeve 52 and stopper 106. Thus, direct fluid communication to the interior of evacuated tube 104 is achieved and an efficient blood flow into evacuated tube will result. Evacuated tube 104 may be removed upon collection of an acceptable volume of blood, and one or more additional evacuated tubes may be inserted into tube receiving chamber 24 for collecting additional samples of blood.

After collection of the last sample of blood, evacuated tube 104 is withdrawn from tube receiving chamber 24. The phlebotomist then simultaneously exerts digital pressure on actuator 92 of trigger 90 while exerting a proximal pulling force on blood collection needle assembly 10. These actions will cause distal needle cannula 70 to be withdrawn from the patient and simultaneously will cause spring 86 to propel distal needle assembly 70 into needle receiving chamber 26 of holder body 14. The evacuated tubes with samples of blood therein then can be shipped to a laboratory for analysis, and the safely shielded blood collection needle assembly 10 may be deposited in a sharps receptacle.

While the invention has been described with respect to a preferred embodiment, it is apparent that various changes can be made without departing from the scope of the invention as defined by the appended claims. For example, the invention has been described specifically for collecting samples of blood. However, the assembly can be adapted for collecting other fluid samples.

What is claimed is:

1. A needle holder assembly for collecting samples of fluid, said assembly comprising:
    a holder body having opposed proximal and distal ends, a tube receiving chamber extending into said proximal end of said holder body and continuing to a distal end wall at said distal end of said holder body, and a needle receiving chamber extending into said distal end of said holder body and continuing to a proximal end wall substantially at said proximal end of said holder body, said proximal end wall including a vent extending therethrough and communicating with said needle receiving chamber;
    a proximal needle cannula having a distal end mounted to said holder body and a proximal end extending into said tube receiving chamber;
    a distal needle cannula having proximal and distal ends, said distal needle cannula being mounted to said holder body for movement between a distal position where said distal end of said distal needle cannula projects beyond said distal end of said holder body and a proximal position where substantially all of said distal needle cannula is within said needle receiving chamber of said holder body;
    a passage for providing fluid communication between said distal needle cannula and said proximal needle cannula when said distal needle cannula is in said distal position;
    a spring for urging said distal needle cannula proximally and into said needle receiving chamber of said holder body;
    a trigger for releasably holding said distal needle cannula in said distal position and against forces exerted by said spring.

2. The needle holder assembly of claim 1, wherein said proximal needle cannula and said distal needle cannula are substantially parallel and offset from one another.

3. The needle holder assembly of claim 2, wherein the passage is a transverse passage extending transversely of said proximal needle cannula and distal needle cannula, at least a portion of said transverse passage being formed from a transparent material for providing visual indication of fluid flowing through said transverse passage.

4. The needle holder assembly of claim 2, wherein said holder body includes a generally tubular outer wall, said distal needle cannula being spaced from said outer wall by a selected distance, said proximal needle cannula being spaced from said outer wall by a distance greater than said selected distance between said distal needle cannula and said outer wall of the holder body.

5. The needle holder assembly of claim 1, further comprising a cap mounted to said distal end of said holder body, said cap including a generally tubular nose having a needle mounting chamber formed therein, said distal needle cannula being slidably mounted in said needle mounting chamber of said nose, said spring being a coil spring surrounding a portion of said distal needle cannula for propelling said distal needle cannula proximally into said needle receiving chamber.

6. The needle holder assembly of claim 1, wherein said trigger includes a locking aperture with a cross-sectionally large portion and a cross-sectionally small portion, said cross-sectionally small portion being dimensioned to enable said trigger to engage said distal needle cannula for holding said distal needle cannula in said distal position, said cross-sectionally large portion being dimensioned for permitting said distal needle cannula to move into said needle receiving chamber in response to forces generated by said spring.

7. The needle holder assembly of claim 1, wherein said holder body comprises an outer wall and an inner wall defining said tube receiving chamber and said needle receiving chamber, said inner wall connecting spaced apart locations on said outer wall and that said inner wall defines portions of both said tube receiving chamber and said needle receiving chamber.

8. The needle holder assembly of claim 1, further comprising a plastic hub mounted to said proximal end of said distal needle cannula, said hub having a proximal seal disposed proximally of said passage when said distal needle cannula is in said distal position for preventing fluid flow into said needle receiving chamber, said hub further comprising a distal seal disposed distally of said passage when said distal needle cannula is in said distal position for preventing flow of fluid from said distal needle cannula to external locations.

* * * * *